United States Patent
Mori et al.

(10) Patent No.: US 8,790,929 B2
(45) Date of Patent: Jul. 29, 2014

(54) REAGENT FOR DILUTING BLOOD SAMPLE AND METHOD FOR MEASURING MEAN CORPUSCULAR VOLUME BY USING THE SAME

(75) Inventors: Yusuke Mori, Kobe (JP); Kinya Uchihashi, Kakogawa (JP); Yasuhiro Sakai, Kobe (JP)

(73) Assignee: Sysmex Corporation, Hyogo (JP)

( * ) Notice: Subject to any disclaimer, the term of this patent is extended or adjusted under 35 U.S.C. 154(b) by 867 days.

(21) Appl. No.: 12/497,952

(22) Filed: Jul. 6, 2009

(65) Prior Publication Data

US 2010/0081161 A1    Apr. 1, 2010

(30) Foreign Application Priority Data

Sep. 26, 2008 (JP) ................................. 2008-247485

(51) Int. Cl.
*G01N 33/48* (2006.01)
(52) U.S. Cl.
USPC ........... 436/63; 436/8; 436/10; 435/2; 435/29
(58) Field of Classification Search
None
See application file for complete search history.

(56) References Cited

U.S. PATENT DOCUMENTS

| | | | |
|---|---|---|---|
| 4,506,018 A | 3/1985 | North, Jr. | |
| 5,951,971 A * | 9/1999 | Kawashima et al. | 424/78.04 |
| 5,958,776 A | 9/1999 | Sakata et al. | |
| 6,225,124 B1 | 5/2001 | Houwen et al. | |
| 2007/0178597 A1 | 8/2007 | Tsuji et al. | |
| 2007/0231913 A1 | 10/2007 | Tsuji et al. | |

FOREIGN PATENT DOCUMENTS

| | | |
|---|---|---|
| EP | 0 844 481 A1 | 5/1998 |
| EP | 1 813 942 A1 | 8/2007 |
| JP | 2000-356636 A | 12/2000 |
| JP | 2007-225595 A | 9/2007 |
| JP | 2007-263894 A | 10/2007 |

OTHER PUBLICATIONS

Yin J. et al., Effects of Antioxidants on the Hydrogen Peroxide-Mediated Oxidation of Methionine Residues in Granulocyte Colony-Stimulating Factor and Human Parathyroid Hormone Fragment 13-34, Pharmaceutical Research, Dec. 2004, vol. 21, No. 12, pp. 2377-2383.*

Roy S. et al., Thermoreversible Gel Formulations Containing Sodium Lauryl Sulfate or n-Lauroylsarcosine as Potential Topical Microbicides against Sexually Transmitted Diseases, Antimicrobial Agents and Chemotherapy, Jun. 2001, vol. 45, No. 6, pp. 1671-1681.*

* cited by examiner

*Primary Examiner* — Satyendra Singh
(74) *Attorney, Agent, or Firm* — Sughrue Mion, PLLC

(57) ABSTRACT

The invention provides a reagent for diluting a blood sample, comprising water, polyoxyethylene alkyl ether having a hydroxyl value of 52 to 60, and an osmo-regulator for regulating the osmotic pressure of the reagent in the range of 150 to 400 mOsm/kg, as well as a method for measuring the mean corpuscular volume of a blood sample.

16 Claims, 6 Drawing Sheets

REAGENT FOR DILUTING BLOOD SAMPLE AND METHOD FOR MEASURING MEAN CORPUSCULAR VOLUME BY USING THE SAME

FIELD OF THE INVENTION

The present invention relates to a reagent for diluting a blood sample and a method for measuring mean corpuscular volume (also referred to hereinafter as MCV) by using the same.

BACKGROUND

An automated hematological analyzer is an apparatus in which the analysis of blood samples is automated. As an item measured by this automated hematological analyzer, there is MCV (mean corpuscular volume) of a blood sample. The MCV is obtained as the hematocrit divided by the red blood cell (also referred to thereinafter as RBC) count. The hematocrit is the percentage of red blood cells in unit volume of whole blood. Accordingly, MCV is a value indicative of the mean volume of red blood cell. MCV is expressed in unit femtoliter (fL) or $10^{-15}$ L.

A sheath flow DC detection method is known as a method of determining RBC count and hematocrit by an automated hematological analyzer. In the sheath flow DC detection method, the number and size of blood cells are measured by detecting a change in impedance generated upon passage of blood cells through a fine pore arranged in a flow cell. When a blood sample is analyzed with this automated hematological analyzer, the blood sample should be diluted with a physiologically isotonic diluent. As general diluents for diluting whole blood, there are physiological saline, Ringer solution, Rocke solution, and Tyrode solution.

A blood sample-diluting reagent described in U.S. Pat. No. 6,225,124 is known as a blood sample-diluting reagent for preventing a change with time in the MCV of a blood sample. The blood sample-diluting reagent described in U.S. Pat. No. 6,225,124 contains at least one nonionic surfactant and a substance for regulating the osmotic pressure of the reagent in the range of about 150 to 400 mOsm/kg.

However, when the blood sample-diluting reagent described in U.S. Pat. No. 6,225,124 is used to measure the MCV of a blood sample, the MCV is changed depending on measurement temperature. More specifically, the MCV is significantly reduced as the temperature increases from low temperature. Then, the MCV has a flexion point at a certain temperature. Then, when the temperature at the flexion point is exceeded, the MCV is gradually increases as the temperature increases.

Generally in measurement of the MCV of a blood sample with an automated hematological analyzer, the measurement temperature is often 20° C. or more. However, the measurement temperature may become less than 20° C., depending on the environment under which the automated hematological analyzer is installed or on the performance of a heater in the automated hematological analyzer. Accordingly, when the flexion point is 20° C. or more, the correction, with measurement temperature, of measurement results from the automated hematological analyzer requires complicated correction. As a result, in measurement of MCV of blood samples with the automated hematological analyzer, there has been a problem that errors in measurement results are caused by measurement temperature.

SUMMARY

The scope of the present invention is defined solely by the appended claims, and is not affected to any degree by the statements within this summary.

An object of the present invention is to provide a blood sample-diluting reagent with reduction in measurement errors attributable to measurement temperature in measurement of MCV of blood samples with an automated hematological analyzer. More specifically, an object of the present invention is to provide a blood sample-diluting reagent having a flexion-point temperature of 20° C. or less at which MCV is changed by measurement temperature.

Another object of the present invention is to provide a method for measuring MCV of blood samples with an automated hematological analyzer with reduction in measurement errors attributable to measurement temperature by using the blood sample-diluting reagent described above.

When the reagent for diluting a blood sample according to the present invention is used, complicated correction is not necessary for making correction, by measurement temperature, of measurement results in measurement of MCV of blood samples with an automated hematological analyzer. Accordingly, measurement results of MCV with reduction in errors generated by measurement temperature can be obtained.

DETAILED DESCRIPTION OF THE EMBODIMENT

Figure 1:
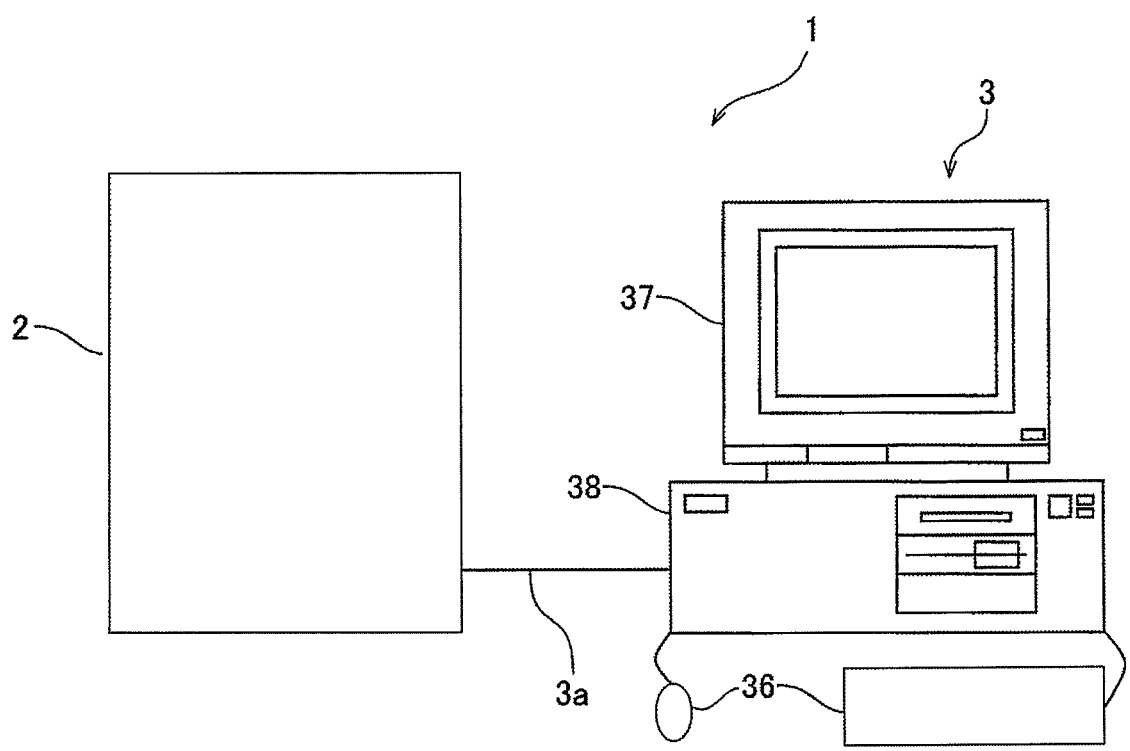
FIG. 1 is a front view showing a skeleton framework of an automated hematological analyzer 1.

The reagent for diluting a blood sample in this embodiment contains water, polyoxyethylene alkyl ether having a hydroxyl value of 52 to 60, and an osmo-regulator, and has an osmotic pressure of 150 to 400 mOsm/kg.

In this embodiment, the hydroxyl value is a numerical value indicative of the degree of hydroxyl value contained in an esterified product. More specifically, the hydroxyl value is indicated in terms of the amount (mg) of potassium hydroxide required for neutralizing acetic acid in an amount necessary for acetylation of free hydroxyl groups contained in 1 g esterified product.

The reagent for diluting a blood sample in this embodiment contains polyoxyethylene alkyl ether having a hydroxyl value of 52 to 60. The reagent preferably contains polyoxyethylene alkyl ether having a hydroxyl value of 53 to 58. The flexion-point temperature at which MCV is changed by measurement temperature can thereby be 20° C. or less.

The hydroxyl value of the polyoxyethylene alkyl ether decreases as the average number of oxyethylene units therein increases. On the other hand, the hydroxyl value increases as the average number of oxyethylene units decreases. For example, the hydroxyl value of polyoxyethylene (20) oleyl ether having 20 oxyethylene units on average is about 50. The hydroxyl value of polyoxyethylene (19) oleyl ether having 19 oxyethylene units on average is about 55. The hydroxyl value of polyoxyethylene (18) oleyl ether having 18 oxyethylene units on average is about 57. The hydroxyl value of polyoxyethylene (16) oleyl ether having 16 oxyethylene units on average is about 60.

The hydroxyl value of the polyoxyethylene alkyl ether can also be regulated by mixing a plurality of polyoxyethylene alkyl ethers different in the average number of oxyethylene units. For example, polyoxyethylene (20) oleyl ether and polyoxyethylene (16) oleyl ether can be mixed at a ratio of 1:3 thereby adjusting the hydroxyl value to about 54. That is, the reagent for diluting a blood sample in this embodiment may contain at least 2 polyoxyethylene alkyl ethers different in the average number of oxyethylene units.

The hydroxyl value of the polyoxyethylene alkyl ether contained in the reagent for diluting a blood sample can be measured by a method known in the art. For example, the polyoxyethylene alkyl ether contained in the reagent for diluting a blood sample is reacted with acetic anhydride in pyridine to form acetic acid. Then, the formed acetic acid can be titrated with potassium hydroxide, with phenolphthalein as an indicator, to determine the hydroxyl value. An automated apparatus for measuring a hydroxyl value is commercially available. This apparatus can be used to measure the hydroxyl value of the polyoxyethylenealkyl ether contained in the reagent for diluting a blood sample. The average number of oxyethylene units in the polyoxyethylene alkyl ether used in this embodiment is preferably 16 or more.

The concentration of the polyoxyethylene alkyl ether contained in the reagent for diluting a blood sample is 0.0005 to 0.5% by weight, preferably 0.001 to 0.1% by weight, more preferably 0.005 to 0.05% by weight.

In this embodiment, the osmotic pressure of the reagent for diluting a blood sample is regulated in the range of 150 to 400 mOsm/kg, preferably 230 to 350 mOsm/kg. By regulating the osmotic pressure of the reagent for diluting a blood sample in this range, a change with time in the MCV of a blood sample can be suppressed. An osmo-regulator for adjusting the osmotic pressure of the reagent for diluting a blood sample to the above-defined osmotic pressure includes, for example, sodium chloride and potassium chloride and the like.

In this embodiment, the reagent for diluting a blood sample can contain a buffer. The buffer includes a phosphate buffer, borate buffer, Tris buffer and imidazole buffer. Particularly, the borate buffer is preferable.

In this embodiment, the pH of the reagent for diluting a blood sample is regulated in the range of 6 to 8.5. The pH adjuster for adjustment to the above pH includes, for example, hydrochloric acid and sodium hydroxide and the like.

In this embodiment, the reagent for diluting a blood sample can contain an oxidant inhibitor. The oxidant inhibitor includes EDTA and butyl methyl phenol and the like. Particularly, EDTA is preferable.

In this embodiment, the reagent for diluting a blood sample can contain antiseptic agent. The antiseptic agent includes sodium 2-pyridylthio-1-oxide and β-phenethyl alcohol. Particularly, sodium 2-pyridylthio-1-oxide is preferable.

FIG. 1 is a front view showing a skeleton framework of an automated hematological analyzer 1 in measuring MCV with the reagent for diluting a blood sample according to the present invention. As shown in FIG. 1, the automated hematological analyzer 1 in this embodiment is composed of a measurement unit 2 and a data processing unit 3. The measurement unit 2 and the data processing unit 3 are connected by a data transmission cable 3a so as to be data-communicable with each other. The processing unit 3 is composed of an input section 36, a display device 37 and a data processing device 38. In the automated hematological analyzer 1, the predetermined measurement of components contained in a blood sample is conducted by the measurement unit 2. The data processing unit 3 executes analytical processing of measurement data obtained in the measurement unit 2. The measurement unit 2 and the data, processing unit 3 can be connected directly to each other with the data transmission cable 3a. Alternatively, the measurement unit 2 and the data processing unit 3 can be connected via a communication network. The communication network includes a leased line using a phone line, wireless LAN, LAN, and Internet and the like.

Figure 2:
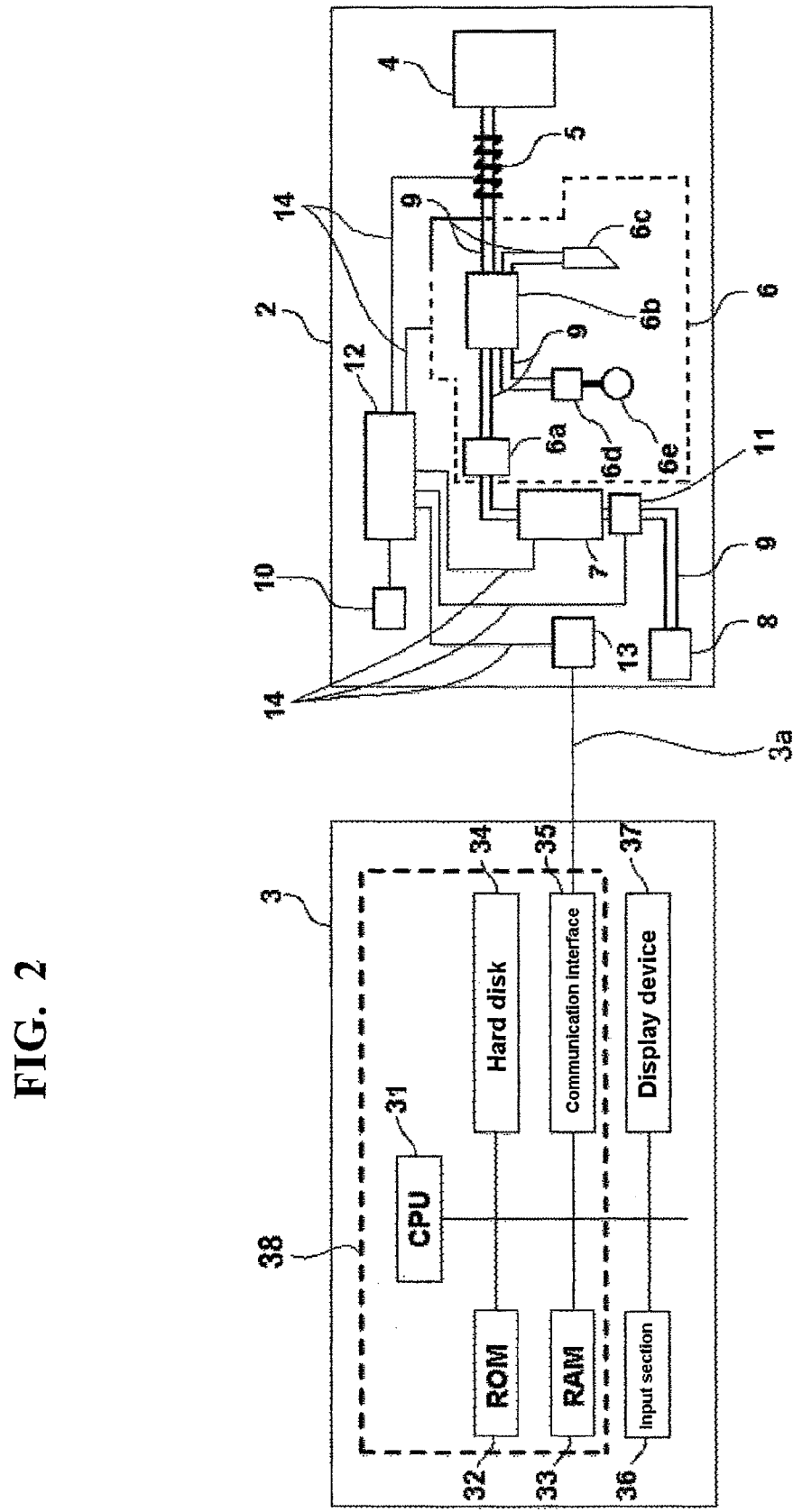
FIG. 2 is a block diagram showing a skeleton framework of the automated hematological analyzer 1.

FIG. 2 is a block diagram showing a skeleton framework of the automated hematological analyzer 1. As shown in FIG. 2, the measurement unit 2 includes a diluent container 4, a heater 5, a sample supply section 6, a DC measurement section 7, a waste chamber 8, a flow path 9, a temperature sensor 10, a temperature sensor 11, a control unit 12 and a communication unit 13.

The reagent for diluting a blood sample (also referred to hereinafter as merely "diluent") is held in the diluent container 4. The sample supply section 6 includes a mixing chamber 6a, a sampling valve 6b, a pipette 6c, a syringe 6d, a motor 6e, and the like.

As shown in FIG. 2, the diluent container 4, the sampling valve 6b, the pipette 6c, the syringe 6d, the mixing chamber 6a, the DC measurement section 7 and the waste chamber 8 are connected to one another via the flow path 9. The movement of a liquid in the flow path 9 is controlled both by the operation of the syringe 6d with the motor 6e and by the sampling valve 6b. More specifically:

(1) A blood sample is suctioned from a blood collection tube via the pipette 6c into the sampling valve.
(2) The blood sample quantified with the sampling valve 6b is diluted 500-fold with the diluent and delivered to the mixing chamber 6a.
(3) The diluted sample in the mixing chamber 6a is sent to the DC measurement section 7.
(4) The diluted sample that has passed through the DC measurement section 7 is discharged into the waste chamber 8.

The measurement unit 2 has the heater 5 on the flow path 9 for connecting the diluent container 4 to the sampling valve 6b. By the heater 5, the diluent is heated so that the temperature of the diluted sample in the DC measurement section 7 reaches 20° C. or more. The heater 5 in the measurement unit 2 is arranged on the flow path 9 for connecting the diluent container 4 to the sampling valve 6b, but this arrangement is not limiting. The heater 5 may be arranged such that the temperature of the diluted sample in the DC measurement section 7 reaches 20° C. or more. For example, the heater 5 may be arranged on an other place of the flow path 9. Alternatively, the heater 5 may be arranged so as to directly heat the diluent container 4 or the mixing chamber 6a.

The temperature sensor 11 is for measuring the temperature of the diluted sample in the DC measurement section 7. The temperature sensor 11 is arranged preferably near to the DC measurement section 7. This is to more accurately measure the temperature of the diluted sample in the DC measurement section 7. The temperature sensor 11 of the measurement unit 2 in this embodiment is arranged so as to measure the temperature of the diluted sample after passage through the DC measurement section 7. However, the temperature sensor 11 may be arranged so as to measure the temperature of the diluted sample before introduction into the DC measurement section 7. Alternatively, the temperature sensor 11 may be arranged so as to measure the temperature of the diluted sample in a flow cell 71 described later in the DC measurement section 7.

The temperature sensor 10 is for measuring the surrounding temperature of the automated hematological analyzer 1. Accordingly, the temperature sensor 10 is disposed preferably where it is hardly influenced by heat generated by the heater 5, the heater 6e and the like. In this example, the temperature sensor 10 of the measurement unit 2 is disposed inside of the measurement unit 2. However, the temperature sensor 10 may be disposed outside of the measurement unit 2.

Figure 3:
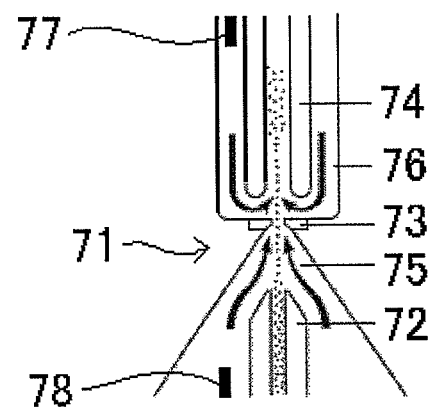
FIG. 3 is a diagram showing a skeleton framework of a flow cell 71.

The DC measurement section 7 has the flow cell 71 to which the diluted sample is to be transferred from the mixing chamber 6a. FIG. 3 is a diagram showing a skeleton framework of the flow cell 71 of the DC measurement section 7. The flow cell 71 has a sample nozzle 72 for supplying the diluted sample to the flow cell, an aperture 73 having a fine pore, a recovery tube 74 for recovering the diluted sample having passed through the aperture 73, a minus electrode 77 and a plus electrode 78. In the flow cell 71, the sample nozzle 72 is disposed before the aperture 73, and both of them have a common center. When the diluted sample is extruded from the sample nozzle 73, the diluted sample is sheathed with a front sheath liquid 75 and passes through the central portion of the aperture 73. The diluted sample, after passage through the aperture 73, is sheathed with a back sheath liquid 76 and sent into the recovery tube 74. DC current flows between the minus electrode 77 and the plus electrode 78. A pulse signal of the DC current changes due to a change in electric resistance caused upon passage of blood cells in the diluted sample through the aperture 73. That is, in the DC measurement section 7, blood cells contained in the diluted sample can be measured as a change in the pulse signal. Based on the pulse signal obtained in the DC measurement section 7, the data processing unit calculates red blood cell (RBC) count and hematocrit (HCT) by a sheath flow DC detection method and a corpuscular pulse high value detection method. More specifically, RBC is calculated based on the number of pulses in the pulse signal, and HCT is calculated based on the height of pulses in the pulse signal.

The communication unit 13 is an interface such as, for example, an RS-232C interface, USB interface and Ethernet (registered trademark). The communication unit 13 is constituted so as to be capable of sending and receiving data to/from the data processing unit 3. The communication unit 13 is connected via a circuit to the control unit 12 and constituted so as to be capable of sending and receiving data to/from the control unit 12.

The control unit 12 is composed of CPU, ROM, RAM and the like. The control unit 12 is connected via the circuit 14 to the respective parts of the measurement unit 2 and constituted to regulate their operation as well as to send and receive data. For example, the control unit 12 controls the operation of the motor 6e for the sample supply section 6, thereby controlling the operation of a liquid in the flow path 9. Further, the control unit 12 transmits data received from the temperature sensor 11, temperature sensor 10, and DC measurement section 7, to the communication unit 13. Furthermore, the control unit 12 also transmits information received from the data processing unit 3 by the communication unit 13, to the respective parts of the measurement unit 2.

As shown in FIG. 2, the data processing unit 3 is composed of a computer including an input section 36 such as a keyboard, a mouse and the like, a display device 37, and a data processing unit 38. The data processing unit 38 is composed of CPU 31, ROM 32, RAM 33, hard disk 34, and communication interface 35. An application program is installed on the hard disk 34 of the data processing unit 3. This application program includes an operating system and a program for analytical processing of measurement data received from the measurement unit 2.

In this embodiment, CPU 31 in the data processing unit 3 is constituted to execute this application program, thereby analyzing measurement data to calculate red blood cell count (RBC), hematocrit value (HCT) and mean corpuscular volume (MCV).

The communication interface 35 is an interface such as, for example, an RS-232C interface, USB interface and Ethernet (registered trademark). The communication interface 35 is constituted so as to be capable of sending and receiving data to/from the measurement unit 2.

Figure 4:
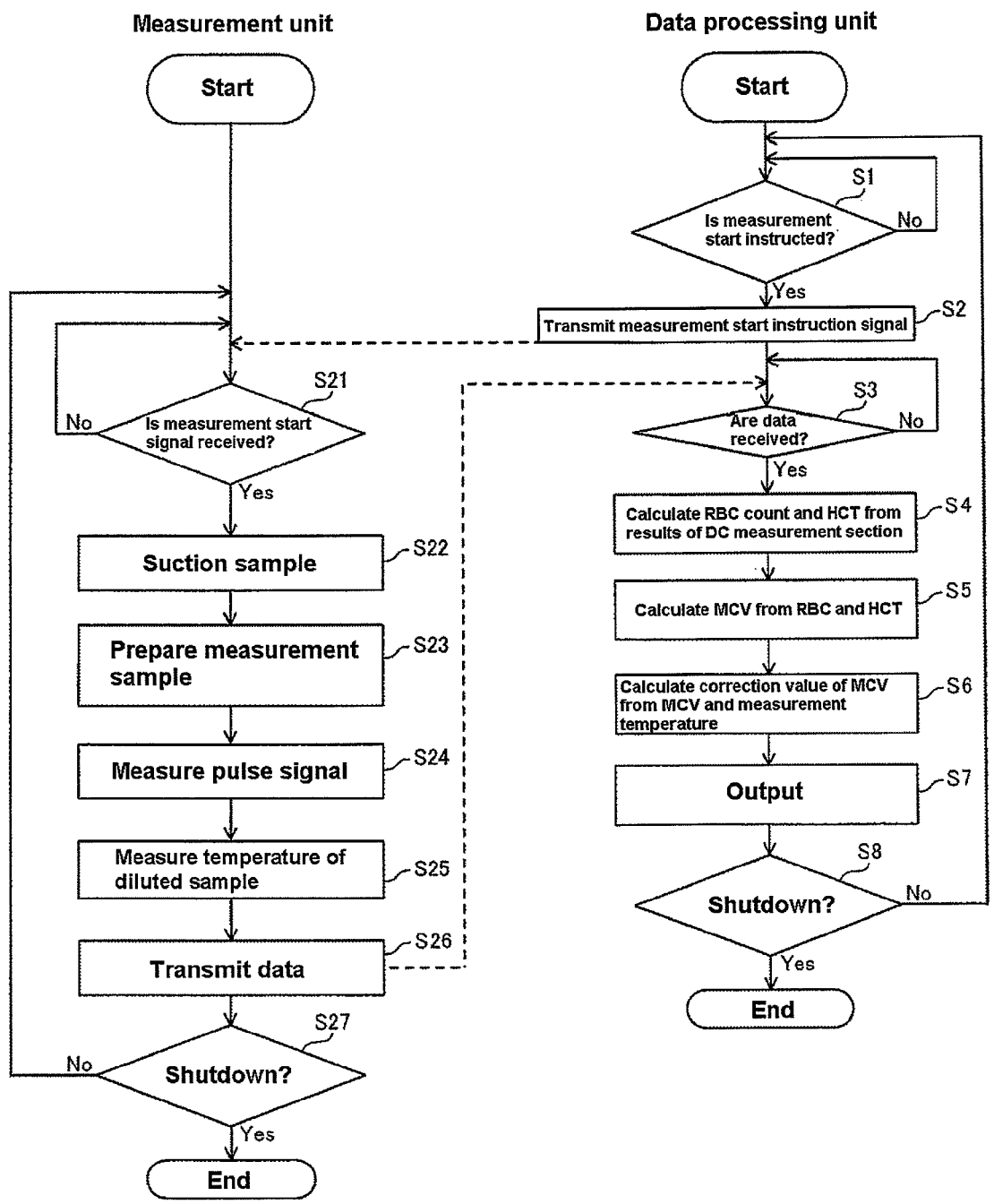
FIG. 4 is a flowchart showing sample analysis processing in the automated hematological analyzer 1.

FIG. 4 is a flowchart showing the sample analysis processing in the automated hematological analyzer 1 shown in FIGS. 1 and 2. Hereinafter, the sample analysis processing in the automated hematological analyzer 1 will be described with reference to FIG. 4.

When the automated hematological analyzer 1 is first started, the application program and the like are initialized. Thereafter, in step S1, whether or not the start of measurement has been instructed by the user is judged with CPU 31 in the data processing unit 3. This judgment is repeated until the start of measurement is instructed. When the start of measurement has been instructed, a signal of the start of measurement is transmitted in step S2 from the data processing unit 3 to the measurement unit 2.

Then, in step S21, whether the signal of the start of measurement has been received or not is judged with the control unit 8 in the measurement unit 2. This judgment is repeated until the signal of the start of measurement is received. When the measurement unit 2 receives the signal of the start of measurement, a blood sample is suctioned via pipette 6c from a blood collection tube, in step S22.

Then, in step S23, a diluted sample is prepared in the sample supply section 6. Specifically, a predetermined amount (for example, 2.0 mL) of a diluent, and a predetermined amount (for example, 4 µL) of the blood sample suctioned via the pipette 6c from the blood collection tube 20, are supplied to, and stirred in, the mixing chamber 6a. The diluent is heated with heater 5 in the flow path 9 from the diluent container 4 to the mixing chamber 6a. By so doing, a predetermined amount (for example, 2.0 mL) of a heated diluted sample is prepared. Thereafter, in step S24, a portion (for example, 1 mL) of the diluted sample in the mixing chamber 6a, together with a sheath liquid (a diluent), is transferred to the DC measurement section 7. Blood cells contained in the diluted sample there bypass through the aperture 73 in the flow cell 71 in the DC measurement section 7. A pulse signal showing a change, generated upon passage of the blood cells through the aperture 73, in the electric resistance of DC current flowing between the minus electrode 77 and plus electrode 78 is measured.

Then, in step S25, the temperature of the diluted sample (measurement temperature) having passed through the DC measuring section 7 is measured with the temperature sensor 11. The heater 5 has been set up such that the measurement temperature reaches 23° C. or more by heating the diluent used in preparation of the diluted sample.

Then, in step S26, measurement data containing the pulse signal and the measurement temperature, measured in the respective detection sections, are transmitted from the measurement unit 2 to the data processing unit 3.

In step S3, whether the measurement data transmitted from the measurement unit 2 have been received or not is judged with the data processing unit 3. This judgment is repeated until the data are received. When the measurement data are received, red blood cell count (RBC) and hematocrit value (HCT) are calculated in step S4 with CPU 31, based on the pulse signal measured in step S24.

Thereafter, in step S5, mean corpuscular volume (MCV) is calculated from the red blood cell count (RBC) and hematocrit value (HCT) with CPU 31 by using the following equation (1):

$$MCV=(HCT/RBC)\times 1000 \quad (1)$$

wherein MCV is mean corpuscular volume (fL), HCT is hematocrit value (%) and RBC is red blood cell count ($\times 10^4$ µL).

Further, in step S6, a correction value of MCV is calculated from the mean corpuscular volume (MCV) and measurement temperature with CPU 31 by using the following equation (2):

$$\text{Corrected MCV}=MCV\times(1+0.048\times(23-\text{measurement temperature})) \quad (2)$$

The corrected MCV obtained by the equation (2) above is MCV with reduction in errors attributable to measurement temperature.

Then, in step S7, the calculation results of red blood cell count (RBC), hematocrit value (HCT), mean corpuscular volume (MCV) and corrected MCV calculated as described above are outputted on the display device 37.

Thereafter, whether or not shutdown has been instructed by the user is judged in step S8. When shutdown is not instructed, the process proceeds to step S1. When shutdown has been instructed, the operation of sample analysis processing by the data processing unit 3 in the automated hematological analyzer 1 is terminated. In the measurement unit 2, the measurement data are transmitted in step S26 to the data processing unit 3, and then, whether or not shutdown has been instructed by the user is judged in step S27. When shutdown is not instructed, the process proceeds to step S21. When shutdown has been instructed, the operation of sample analysis processing by the measurement unit 2 in the automated hematological analyzer 1 is terminated.

In this example, the temperature of the diluent (measurement temperature) measured with the temperature sensor 11 is used to calculate a correction value of MCV. However, the present invention is not limited thereto, and the surrounding temperature (ambient temperature) of the automated hematological analyzer 1, measured with the temperature sensor 10, can be used to calculate a correction value of MCV. Further, both the measurement temperature and the ambient temperature can be used to calculate a correction value of MCV.

Hereinafter, the present invention will be described in detail with reference to the Examples, but the present invention is not limited thereto.

EXAMPLE

Example 1

Preparation of Reagents for Diluting a Blood Sample 2.20 g of sodium chloride was added to 1 L of CELLPACK (manufactured by Sysmex Corporation) as a reagent for diluting a blood sample. Polyoxyethylene oleyl ethers different in hydroxyl value were added to a concentration of 0.015% by weight to the CELLPACK to which sodium chloride had been added, to prepare reagents A to E respectively.

The hydroxyl values of the polyoxyethylene oleyl ethers used in preparation of reagents A to E are shown below.
Reagent A: polyoxyethylene oleyl ether having a hydroxyl value of 49.0
Reagent B: polyoxyethylene oleyl ether having a hydroxyl value of 51.0
Reagent C: polyoxyethylene oleyl ether having a hydroxyl value of 53.6
Reagent D: polyoxyethylene oleyl ether having a hydroxyl value of 54.8
Reagent E: polyoxyethylene oleyl ether having a hydroxyl value of 57.1
(Measurement of MCV)

Figure 5:
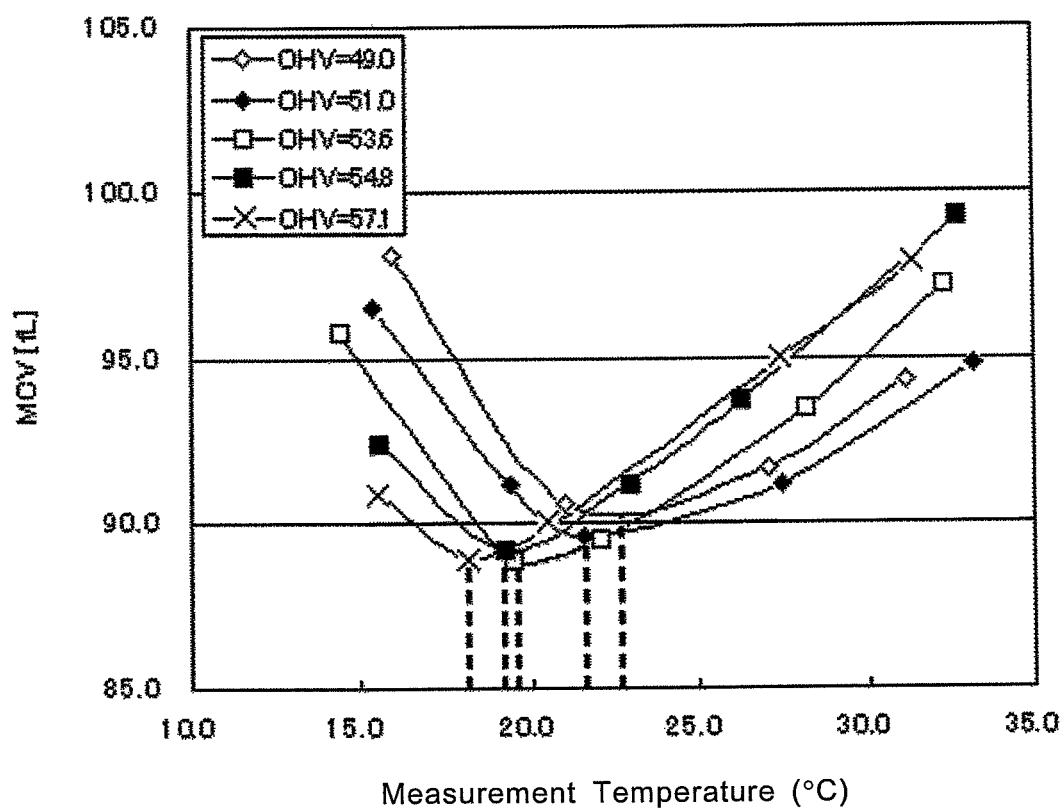
FIG. 5 is a graph showing the relationship between measurement temperatures and measured values of MCV, where reagents A to E are used as reagents for diluting a blood sample.

Each of 3 normal fresh blood samples was diluted 500-fold with each of reagents A to E to prepare a measurement sample. This prepared measurement sample was measured for its MCV at a varying measurement temperature with an automated hematological analyzer XE-2100 (manufactured by Sysmex Corporation). The automated hematological analyzer XE-2100 is not provided with a heater for regulating the temperature of a measurement sample. Hence, the measurement temperature was regulated by changing the surrounding temperature (ambient temperature) of the apparatus. The mean value of measured MCV in the 3 normal fresh blood samples was used as the measured value. FIG. 5 shows the relationship between measurement temperatures and measured values of MCV, where each of the reagents A to E is used as the reagent for diluting a blood sample.

It is evident from FIG. 5 that when the reagent A or B is used as the reagent for diluting a blood sample, the flexion-point temperature is higher than 20° C. When the reagent C, D or E is used as the reagent for diluting a blood sample, on the other hand, the flexion-point temperature is 20° C. or less.

From this result, it was revealed that when the reagent for diluting a blood sample, which contains polyoxyethylene oleyl ether having a hydroxyl value of 53.6 or more, is used, the MCV of a blood sample can be measured with the automated hematological analyzer without necessity for complicated correction as long as the measurement temperature is 20° C. or more.

Example 2

Preparation of a Reagent for Diluting a Blood Sample

A mixture consisting of polyoxyethylene (20) oleyl ether and polyoxyethylene (16) oleyl ether in a ratio of 1:3 was added to a concentration of 0.015% by weight to CELLPACK (II) (manufactured by Sysmex Corporation) as a reagent for diluting a blood sample, to prepare a blood sample-diluting reagent having a hydroxyl value of 54.
(Measurement of MCV and Correction of Measured Values)

Three normal fresh blood samples were diluted 500-fold respectively with the blood sample-diluting reagent having a hydroxyl value of 54, to prepare measurement samples. The prepared measurement samples were measured for their MCV at ambient temperature with the automated hematological analyzer XE-2100 (manufactured by Sysmex Corporation). The results are shown in black squares (■) in FIG. 6.

Separately, the measurement samples were measured for their MCV at a temperature regulated at 23° C. or more with an automated hematological analyzer XE-2100C (manufactured by Sysmex Corporation). The results are shown in black circles (●) in FIG. 6. The automated hematological analyzer XE-2100C is an apparatus consisting of the automated hematological analyzer XE-2100 provided with a heater for heating the reagent for diluting a blood sample. More specifically, the automated hematological analyzer XE-2100C, similar to the automated hematological analyzer 1 shown in FIG. 2, is provided with a heater in a flow path with which a diluent container for holding the reagent for diluting blood sample is connected to a sampling valve.

Figure 6:
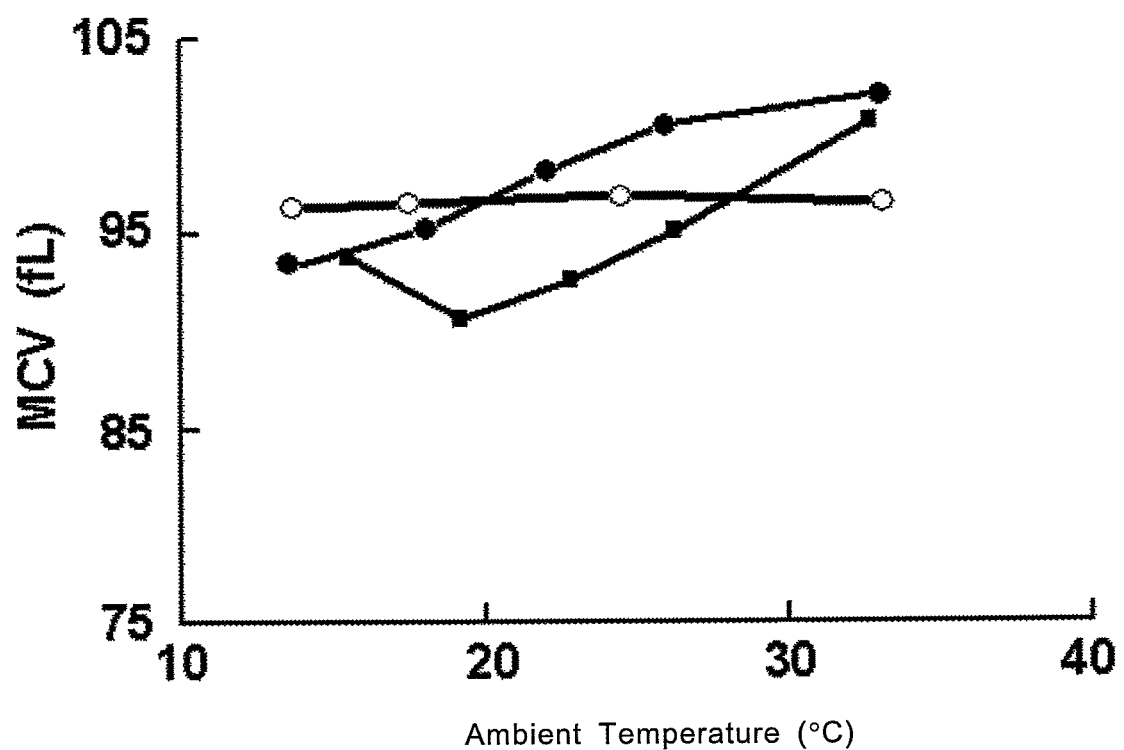
FIG. 6 is a graph showing measurement results (■) of MCV measured at ambient temperature, measurement results (●) of MCV measured at a measurement temperature regulated at 23° C. or more, and correction values (○) of MCV measured at a measurement temperature regulated at 23° C. or more and corrected at the measurement temperature.

Corrected MCV obtained by correcting, by the above equation (2) with the measurement temperature, the results of the measurement sample measured at a measurement temperature regulated at 23° C. or more by heating the blood sample-diluting reagent with the heater are shown in (○) in FIG. 6.

The mean value of measured MCV in the 3 normal fresh blood samples was used as the measured value.

As is evident from FIG. 6, the measured value of MCV can be monotonically increased by using the blood sample-diluting reagent having a hydroxyl value of 54 while regulating the measurement temperature at 23° C. or more. Accordingly, it was revealed that the simple primary expression represented by the equation (2) can be used to accurately correct the measured value of MCV.

The foregoing detailed description and examples have been provided by way of explanation and illustration, and are not intended to limit the scope of the appended claims. Many variations in the presently preferred embodiments will be obvious to one of ordinary skill in the art, and remain within the scope of the appended claims and their equivalents.

What is claimed is:

1. A reagent for diluting a blood sample for measuring the mean corpuscular volume of the blood sample, comprising:
   water,
   a mixture of polyoxyethylene oleyl ethers having a hydroxyl value in the range of 53 to 58, and
   an osmo-regulator for regulating the osmotic pressure of the reagent in the range of 150 to 400 mOsm/kg,
   wherein said mixture consists of polyoxyethylene (16) oleyl ether and polyoxyethylene (20) oleyl ether.

2. The reagent according to claim 1, wherein the concentration of the polyoxyethylene oleyl ethers in said mixture is 0.0005 to 0.5% by weight.

3. The reagent according to claim 1, wherein the osmotic pressure of the reagent is in the range of 230 to 350 mOsm/kg.

4. The reagent according to claim 1, wherein the osmo-regulator is sodium chloride.

5. The reagent according to claim 1, wherein pH of the reagent is in the range of 6 to 8.5.

6. The reagent according to claim 1 further comprising a buffer.

7. The reagent according to claim 1 further comprising a pH adjuster.

8. The reagent according to claim 1 further comprising an oxidant inhibitor.

9. The reagent according to claim 1 further comprising an antiseptic agent.

10. A method for measuring the mean corpuscular volume of a blood sample, comprising steps of:
    diluting the blood sample with a reagent comprising water, a mixture of polyoxyethylene oleyl ethers having a hydroxyl value in the range of 53 to 58, and an osmo-regulator for regulating the osmotic pressure of the reagent in the range of 150 to 400 mOsm/kg, wherein said mixture consists of polyoxyethylene (16) oleyl ether and polyoxyethylene (20) oleyl ether;
    supplying the diluted sample obtained by the diluting step to a flow cell having a fine pore;
    measuring blood cells contained in the diluted sample passing through the fine pore; and
    calculating the mean corpuscular volume of the blood sample based on the measurement result of blood cells obtained in the blood cell measuring step.

11. The method according to claim 10 further comprising a step of measuring temperature of the diluted sample,
    wherein the calculating step comprises calculating the mean corpuscular volume of the blood sample based on the measurement result of the blood cells and the temperature of the diluted sample.

12. The method according to claim 11, wherein the temperature of the diluted sample is the temperature of the diluted sample before supplying to the flow cell.

13. The method according to claim 11, wherein the temperature of the diluted sample is the temperature of the diluted sample after passage through the flow cell.

14. The method according to claim 11, wherein the temperature of the diluted sample is the temperature of the diluted sample in the flow cell.

15. The method according to claim 10, wherein temperature of the diluted sample supplied to the flow cell is not less than 20° C.

16. The method according to claim 10 further comprising a step of measuring ambient temperature,
    wherein the calculating step comprises calculating the mean corpuscular volume of the blood sample based on the measurement result of the blood cells and the ambient temperature.

* * * * *